(12) United States Patent
Chefitz

(10) Patent No.: US 11,291,408 B2
(45) Date of Patent: Apr. 5, 2022

(54) EYEWEAR SYSTEM FOR DETECTING AND INDICATING PRESENCE OF CORONAVIRUS

(71) Applicant: 123IV, Inc., New Rochelle, NY (US)

(72) Inventor: Allen B. Chefitz, New Rochelle, NY (US)

(73) Assignee: 123IV, Inc., New Rochelle, NY (US)

( * ) Notice: Subject to any disclaimer, the term of this patent is extended or adjusted under 35 U.S.C. 154(b) by 0 days.

(21) Appl. No.: 17/381,058

(22) Filed: Jul. 20, 2021

(65) Prior Publication Data
US 2022/0015700 A1    Jan. 20, 2022

Related U.S. Application Data

(60) Provisional application No. 63/053,808, filed on Jul. 20, 2020.

(51) Int. Cl.
| | |
|---|---|
| G01N 33/569 | (2006.01) |
| G02C 7/16 | (2006.01) |
| G01N 33/543 | (2006.01) |
| A61B 5/00 | (2006.01) |
| A61B 5/1477 | (2006.01) |
| A61B 5/145 | (2006.01) |
| G02C 11/00 | (2006.01) |
| G02C 5/12 | (2006.01) |
| A61B 10/00 | (2006.01) |

(52) U.S. Cl.
CPC .......... *A61B 5/6803* (2013.01); *A61B 5/1477* (2013.01); *A61B 5/14507* (2013.01); *A61B 5/14546* (2013.01); *G01N 33/54388* (2021.08); *G01N 33/56983* (2013.01); *G02C 5/12* (2013.01); *G02C 7/16* (2013.01); *G02C 11/00* (2013.01); *A61B 2010/0067* (2013.01); *G01N 2469/10* (2013.01); *G01N 2800/26* (2013.01)

(58) Field of Classification Search
CPC ............ A61B 5/14507; A61B 5/14546; A61B 5/1477; A61B 2010/0067; G01N 33/54388; G01N 33/56983; G01N 2469/10; G01N 2800/26; G02C 5/12; G02C 7/16; G02C 11/00
See application file for complete search history.

(56) References Cited

FOREIGN PATENT DOCUMENTS

WO    WO-2021084488 A1 *  5/2021  ........... A61B 5/6803

OTHER PUBLICATIONS

Sempionatto, et al. "Eyeglasses-based tear biosensing system: Non-invasive detection of alcohol, vitamins and glucose," Biosensors and Bioelectronics, 137 (2019) 161-170.

* cited by examiner

*Primary Examiner* — Dennis White
(74) *Attorney, Agent, or Firm* — David H. Judson

(57) ABSTRACT

An article of manufacture comprises an optical shade configured for removable attachment to eyewear, e.g., eyeglasses that are retrofitted to include a micro-fluidic tear collector in a nose pad. The optical shade comprises a lens having a lateral flow assay comprising an antibody having an associated fluorescent tag. The fluorescent tag is configured to fluoresce and change a color of the lens upon detection by the flow assay of an antigen that matches the antibody. The antigen comprises viral constituents, such as SARS-CoV-2. The color change of the lens is visible and indicates presence of Covid-19 infection.

14 Claims, 2 Drawing Sheets

EYEWEAR SYSTEM FOR DETECTING AND INDICATING PRESENCE OF CORONAVIRUS

TECHNICAL FIELD

The subject matter herein relates to diagnostic devices and related methods configured for self-administered, non-invasive, real-time detection of virus, such as SARS-CoV-2 virus, and influenza virus.

BRIEF DESCRIPTION OF THE RELATED ART

Covid-19 (C-19) is a positive single-stranded RNA genome that contains 29891 nucleotides, encoding for 9860 amino acids. The genome is 30 kb in length, the largest of many viruses. Targets for identification include the virus structure, proteins and antibodies. Typically, a definitive Covid-19 infection typically is diagnosed by laboratory tests, including real-time Polymerase Chain Reaction (PCR)-based testing, and serological testing is now also available for detecting SARS-CoV-2 antibodies in a patient's blood. These currently available approaches are invasive.

Further, and although each individual may know their own status as either harboring a virus or not, those around that particular individual—whether on a walk, at work, at school, or anywhere—may also want to know the individual's status, namely, is the individual carrying an infection, or not? In particular, and because we are dealing with an infectious disease that by its very nature can affect and infect others within a certain distance, and by extension any secondary contacts, a testing approach that alerts regarding another's infectivity would provide significant advantages in reducing the overall viral spread.

BRIEF SUMMARY

A technique for detecting and indicating presence of a virus (such as SARS-CoV-2) is associated with a wearable, such as eyewear that includes an embedded collector (e.g., in a nose pad) that collects tears through lateral flow from the wearer's lacrimal duct. An eyewear accessory, such as a clip-on optical shade, includes first and second lens, at least one of which is clear and that supports a flow assay, e.g., a lateral flow assay, comprising an antibody having an associated fluorescent tag (also known as a fluorescent label or probe). In an alternative embodiment, the flow assay is supported on a surface of the shade lens. A fluorescent tag is a molecule that is attached chemically to aid in the detection of a biomolecule such as a protein, antibody, or amino acid. In this approach, the tag primer is a DNA sequence or antibody that matches a virus or viral component of interest, e.g., the SARS-CoV-2 RNA encoding the spike protein, or the spike protein itself, as a target. The fluorescent antibody is specific to any antigen (the virus or other viral constituents of interest) that may be present in the user's tears. When the output of the collector is applied to the flow assay, an antibody-antigen match triggers the tag to fluoresce. Depending on the type of tag, the lens changes color to indicate the presence of the target in the user's tear.

According to a more specific aspect, an article of manufacture comprises an accessory configured for removable attachment to eyewear, e.g., eyeglasses that are retrofitted to include a micro-fluidic tear collector in a nose pad. The accessory comprises a lens having a linear flow assay comprising an antibody having an associated fluorescent tag. The fluorescent tag is configured to fluoresce and change a color of the surface upon detection by the flow assay of an antigen that matches the antibody. The antigen comprises viral constituents, such as SARS-CoV-2. The color change of the lens is visible and indicates presence of Covid-19 infection.

The foregoing has outlined some of the more pertinent features of the subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the subject matter and the advantages thereof, reference is now made to the following descriptions taken in conjunction with the accompanying drawings, in which.

DETAILED DESCRIPTION

Figure 1:
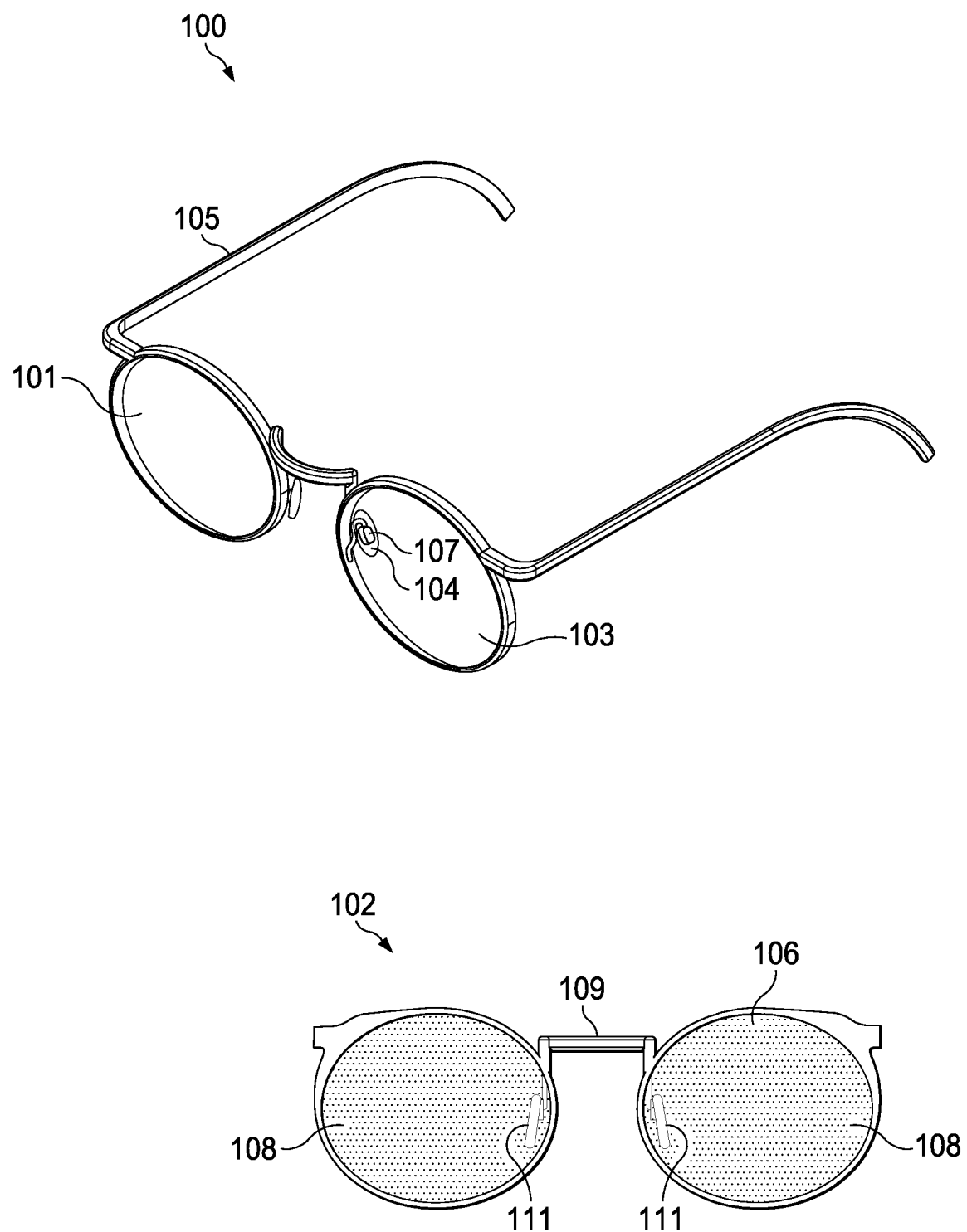
FIG. 1 is a diagram depicting eyewear and an associated optical shade.

As depicted in FIG. 1, an optical shade 102 is associated with eyewear 100. The shade 102 is configured for removable attachment to the eyewear 100, typically via a clip-on (mechanical) attachment in a known manner. The particular manner by which the optical shade is attachable to the eyewear is not a limitation, and the shade may be fixedly attached to the eyewear. The eyewear 100 comprises a pair of lenses 101 and 103 supported by a frame 105 comprising a bridge piece, and left and right temples. The frame 105 also supports nose bridge pads 104. At least one nose bridge pad 104 is retrofitted (or provided as an original element) to support a collector 107 that collects a user's tears non-invasively. The collector may be mounted elsewhere on the eyeglass frame, although the nose pad support is preferred. A representative collector comprises a micro-fluidic element, such as a super-hydrophilic carbonate membrane that acts as a capillary absorbent to receive and collect tear(s). As will be described below, the optical shade 102 (or, more generally, an "accessory") is configured to provide a visual indication of the presence of a biomarker in the collected tears. As depicted in FIG. 1, this indication is a change of color 106 in one or both of the lenses 108 that comprise the optical shade. The lenses 108 of the optical shade are supported by a frame/bridge element 109, and each lens 108 has an associated nose pad or extension 111. Preferably one or both of the lenses 108 change color (typically from a clear initial state) to provide a visual indication of the presence of a particular biomarker (e.g., an antigen) of interest in the tears. The detection approach preferably uses a biochemical detection, which is now described.

Figure 2:
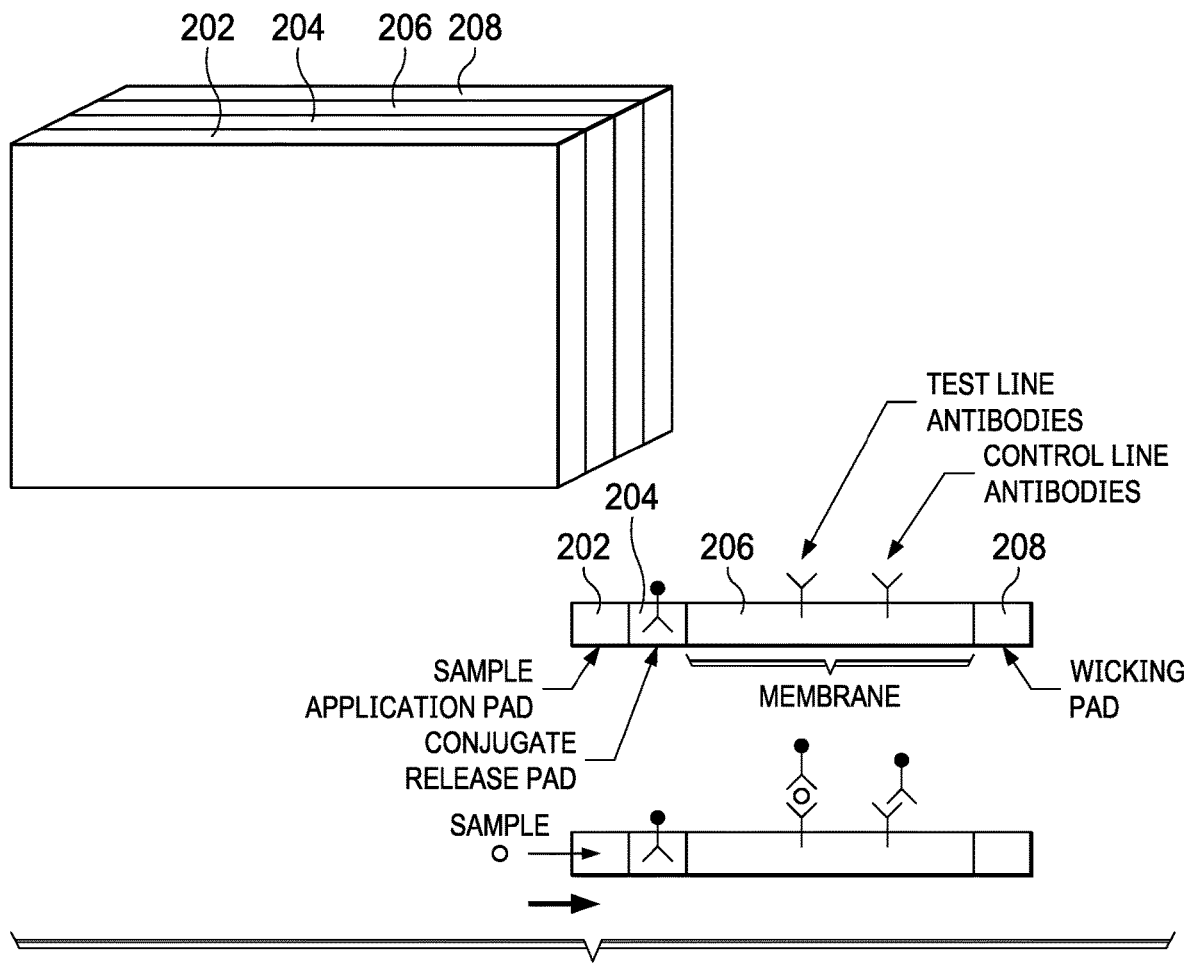
FIG. 2 depicts a lateral flow assay built-into the optical shade lens.

In particular, and as depicted in FIG. 2, at least one of the lenses in the optical shade has a built-in lateral flow assay comprising a set of layers. When viewed front-to-back (or vice versa), these layers comprise a sample application pad 200, a conjugate release pad 202 that contains the tagged antibody, a membrane 204, and a wicking pad 206. The membrane 204 includes a test line that contains an untagged antibody that, with added antigen in a sample, conjugates to both antigen (virus) and the tagged antibody in a sandwich assay, and a control line that is devoid of viral antigen, and a wicking pad 208. As can be seen, preferably the layers 200, 202, 204 and 206 extend width-wise and comprise the lens itself. This is not a requirement, as the lens may support a separate (distinct) assay. The assay performs a lateral flow test (LFT). In particular, the test runs the sample through a series of capillary beds, such as pieces of porous paper, micro-structured polymer or sintered polymer, Each of these pads has the capacity to transport fluid (here, tears) spontaneously. The sample pad 200 acts as a sponge and holds an excess of sample fluid. Once soaked, the fluid flows to the conjugate pad 202 in which are stored freeze dried bioactive particles called conjugates, e.g., in a salt-sugar matrix. The conjugate pad 202 contains all the reagents required for an optimized chemical reaction between the target molecule (e.g., an antigen) and its chemical partner (e.g., antibody) that has been immobilized on the particle's surface. This marks target particles as they pass through the pad and continue across to the test and control lines. The test line shows a signal, often a color. The control line contains affinity ligands that show whether the sample has flowed through and the bio-molecules in the conjugate pad are active. After passing these reaction zones, the fluid enters the final porous material, the wick 208, that simply acts as a waste container.

An alternative embodiment may use a competitive assay.

Figure 3:
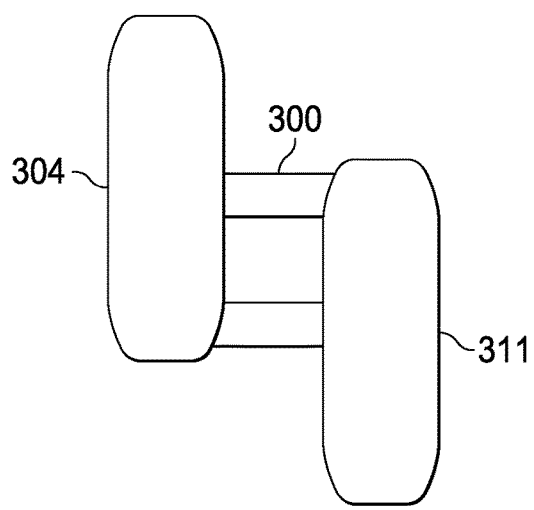
FIG. 3 depicts how tear material is channeled from the eyeglass nose pad to the optical shade flow assay.

As noted above, the detection process herein involves channeling the tear(s) from the eyeglass nose pad 104 to the flow assay, wherein the sample is then analyzed for the presence (or absence) of a biomarker. FIG. 3 depicts one approach for channeling the fluid. In this example embodiment, the nose pad 304 of the eyewear is aligned and closely juxtaposed adjacent nose pad 311 of the shade (when the shade is attached to the eyewear). The nose pad 311 is fitted with one or more micro-fluidic tubes 300 that wick the fluid across the pads. This juxtaposition enables the tear(s) to move, e.g., by capillary action, to the flow assay for evaluation. The pad 311 in the shade is in fluid communication with the flow assay sample pad layer, and thus there is fluid uptake from the shade nose pad and into the assay. Other structures for enabling uptake of the fluid may be used, and the pads 304 and 311 may be in direct communication with one another when the shade is attached.

The particular assay is uniquely associated with a target molecule, thus, the optical shade typically is provided as a set of such shades, with each shade associated with the particular biomarker. The fluorescent tag is configured to fluoresce and change a color of the surface upon detection by the flow assay of an antigen that matches the antibody. This detection results in the color change as depicted in FIG. 1. This juxtaposition enables the fluid to move, e.g., by capillary action, to the flow assay for evaluation.

The particular biomarker may vary. In one embodiment, an antigen of interest is SARS-CoV-2, but this is not a limitation. The above-described optical shade and its detection technique may be used for other antigens.

Generalizing, the approach herein involves integrating a collector element into an eyewear nose pad for non-invasive monitoring of a tear biomarker, such as an antigen indicating of Covid-19 infection. The collector collects and transports the tear to a flow assay supported on a surface associated with an indicator. The indicator is provided in the form of an optical shade, which provides a color change triggered by a fluorescent tag, which is a molecule that is attached chemically to aid in the detection of a biomolecule of interest, such as a protein, antibody, or amino acid. As is known in the art, fluorescent tagging, or labeling, uses a reactive derivative of a fluorescent molecule known as a fluorophore. The fluorophore selectively binds to a specific region or functional group on the target molecule and can be attached chemically or biologically. Various labeling techniques such as enzymatic labeling, protein labeling, and genetic labeling are widely utilized. Ethidium bromide, fluorescein and green fluorescent protein are common tags. The most commonly labelled molecules are antibodies, proteins, amino acids and peptides which are then used as specific probes for detection of a particular target.

The technique provides significant advantages. No electronics or other optical components are required. The approach is integrated in a well-known consumer product (eyewear). Once the test indicates the presence of the biomarker, one is able to "see" the infection, whenever it is in the user's or an observer's line of sight. Because the wearable changes colors when the virus is detected, both the wearer and an observer are able to identify those positive for carrying and harboring a specific virus or infectious agent. The wearable sensor for viral detection simply needs to indicate the presence or absence of the infectious agent. Precise quantification is not as necessary, especially for mass screening.

As noted above, in a preferred embodiment, the lens (similar to removable sun shades) or eyewear contains an antibody-coated surface (e.g., an antibody produced with recombinant DNA technology specific to a given viral agent) targeting the spike protein RNA on the SARS-CoV-2. The tears from the lacrimal duct are drawn into the collector (using micro-fluidic or test strip technology), and the spike protein RNA is isolated and combined with the embedded DNA primer on the shade surface, thereby emitting a color. Fluorescence tags applied to the antibody-coated surface accomplish the color change. The specific target viral RNA may be spliced using CRISPR technology.

There is no requirement that the entire lens be primed with the fluorescent material. Any portion of the optical shade may be triggered for the color change, as long as the portion is sufficiently large enough to enable visual detection. Also, while in the preferred embodiment the assay is a lateral flow assay that is structured across the front-to-back extent of the lens, this is not a requirement. The assay may comprise a portion of the lens, or be positioned on a surface of other lens material.

The approach herein may be extended for use with any wearable device. A wearable devices (or "wearables") are products controlled by electronic components and software that can be incorporated into clothing or worn on the body like accessories. Nowadays, a variety of wearable devices, such as smart glasses and smartwatches, are well-known. More generally, wearable technology, wearables, fashion technology, smartwear, tech togs, skin electronics or fashion electronics are smart electronic devices that are worn close to and/or on the surface of the skin, where they detect, analyze, and transmit information concerning body signals, e.g., such as vital signs, and/or ambient data and which allow in some cases immediate biofeedback to the wearer. Wearable devices such as activity trackers are an example of the Internet of Things, because "things" such as electronics, software, sensors, and connectivity are effectors that enable objects to exchange data (including data quality) through the internet with a manufacturer, operator, and/or other connected devices, without requiring human intervention.

What is claimed follows below:

1. An article of manufacture, comprising:
   an optical shade comprising a lens supporting a flow assay, the flow assay comprising an antibody having an associated fluorescent tag, the shade configured for removable attachment to eyewear, the fluorescent tag configured to fluoresce and change a color of the lens upon detection by the flow assay of an antigen that matches the antibody.

2. The article of manufacture as described in claim 1 wherein the optical shade comprises a nose pad that receives and channels a tear to the flow assay.

3. The article of manufacture as described in claim 1 wherein the antigen comprises viral constituents.

4. The article of manufacture as described in claim 3 wherein the viral constituents comprise SARS-CoV-2.

5. The article of manufacture as described in claim 1 wherein the flow assay is uniquely associated with the antigen.

6. The article of manufacture as described in claim 1 wherein the color change of the lens is visible and indicates presence of Covid-19 infection.

7. The article of manufacture as described in claim 1 wherein the flow assay is a lateral flow assay configured across a width of the lens.

8. An eyewear system, comprising:
   eyewear;
   an optical shade configured for removable attachment to the eyewear;
   the eyewear comprising a micro-fluidic collector integrated into a nose pad and configured to collect, non-invasively, a tear; and
   the optical shade comprising a lens supporting a flow assay, the flow assay comprising an antibody having an associated fluorescent tag, the fluorescent tag configured to fluoresce and change a color of the lens upon detection by the flow assay of an antigen that matches the antibody.

9. The system as described in claim 8 wherein the optical shade comprises a nose pad that receives and channels the tear to the flow assay.

10. The system as described in claim 8 wherein the antigen comprises viral constituents.

11. The system as described in claim 10 wherein the viral constituents comprise SARS-CoV-2.

12. The system as described in claim 8 wherein the flow assay is uniquely associated with the antigen.

13. The system as described in claim 8 wherein the color change of the lens is visible and indicates presence of Covid-19 infection.

14. The system as described in claim 8 wherein the flow assay is a lateral flow assay configured across a width of the lens.

* * * * *